(12) United States Patent
Hartley et al.

(10) Patent No.: US 7,909,863 B2
(45) Date of Patent: Mar. 22, 2011

(54) RETENTION OF EXPOSED STENT LOOPS

(75) Inventors: David Ernest Hartley, Subiaco (AU); Erik E. Rasmussen, Slagelse (DK)

(73) Assignees: Cook Incorporated, Bloomington, IN (US); William Cook Europe APS, Bjaeverskov (DK); William A. Cook Australia Pty, Ltd., Brisbane, Queensland (AU)

( * ) Notice: Subject to any disclaimer, the term of this patent is extended or adjusted under 35 U.S.C. 154(b) by 175 days.

(21) Appl. No.: 11/710,718

(22) Filed: Feb. 26, 2007

(65) Prior Publication Data

US 2008/0027529 A1 Jan. 31, 2008

Related U.S. Application Data

(60) Provisional application No. 60/777,106, filed on Feb. 27, 2006.

(51) Int. Cl.
*A61F 2/06* (2006.01)
*A61F 11/00* (2006.01)

(52) U.S. Cl. ............ 623/1.13; 623/1.11; 623/1.12; 623/1.2; 623/1.23; 606/108

(58) Field of Classification Search .......... 623/1.11–1.3, 623/1.351, 1.13, 1.15, 1.16, 1.27, 1.28, 1.35, 623/1.36; 606/191, 192, 194, 195
See application file for complete search history.

(56) References Cited

U.S. PATENT DOCUMENTS

| | | | | |
|---|---|---|---|---|
| 4,665,918 A | * | 5/1987 | Garza et al. | 606/108 |
| 5,507,771 A | * | 4/1996 | Gianturco | 606/198 |
| 5,569,204 A | * | 10/1996 | Cramer | 604/164.1 |
| 5,720,776 A | * | 2/1998 | Chuter et al. | 623/1.36 |
| 6,221,102 B1 | * | 4/2001 | Baker et al. | 623/1.36 |
| 6,699,274 B2 | * | 3/2004 | Stinson | 623/1.12 |
| 2002/0052644 A1 | * | 5/2002 | Shaolian et al. | 623/1.13 |
| 2002/0143383 A1 | * | 10/2002 | Parodi | 623/1.11 |
| 2003/0233140 A1 | * | 12/2003 | Hartley et al. | 623/1.11 |
| 2004/0102838 A1 | * | 5/2004 | Killion et al. | 623/1.16 |
| 2004/0106974 A1 | * | 6/2004 | Greenberg et al. | 623/1.11 |

(Continued)

FOREIGN PATENT DOCUMENTS

EP 1029517 A2 8/2000

(Continued)

*Primary Examiner* — David Isabella
*Assistant Examiner* — Michael J Booth
(74) *Attorney, Agent, or Firm* — Brinks Hofer Gilson & Lione

(57) ABSTRACT

A stent graft (10) is retained on an introducer (38) by retention of an exposed stent (16) of the stent graft to the introducer with trigger wires (44). The introducer has a trigger wire catheter (40) and four trigger wires and each trigger wire extending in a loop from the trigger wire catheter. The stent graft has a tubular body (12) of a graft material and an exposed stent joined to and extending from one end of the tubular body. The exposed stent is a self expanding Z stent with struts (20) and bends (22, 28, 30) between them. A pair of struts and a bend between define an apex a selected distance to the bend away from the tubular body. Adjacent apices of the exposed stent are different distances to the bends from the tubular body so that they stack under the trigger wires in an neat fashion. Distally extending barbs (26) on alternate struts of the exposed stent are spaced selected distances from their respective apices to prevent tangling during deployment.

6 Claims, 3 Drawing Sheets

U.S. PATENT DOCUMENTS

2004/0230287 A1* 11/2004 Hartley et al. .............. 623/1.12
2005/0049667 A1* 3/2005 Arbefeuille et al. ......... 623/1.11
2005/0149168 A1 7/2005 Gregorich
2006/0136046 A1* 6/2006 Hartley et al. .............. 623/1.35

FOREIGN PATENT DOCUMENTS

WO    WO03/101518 A1    12/2003
WO    WO2005/058202 A1    6/2005

* cited by examiner

RETENTION OF EXPOSED STENT LOOPS

CROSS-REFERENCE TO RELATED APPLICATIONS

This application claims priority of provisional application Ser. No. 60/777,106, filed Feb. 27, 2006.

TECHNICAL

This invention relates to a medical device, and more particularly to an introducer system and retention of a stent graft onto an introducer system.

BACKGROUND OF THE INVENTION

For the endovascular introduction of stent grafts into the human or animal body, there have been proposed introducers or deployment devices which hold such stent grafts in a radially compressed or constrained condition on the introducer and normally upon withdrawal of a sheath and activation of a suitable release mechanism such a stent graft can be released into a body lumen.

Some stent grafts include an exposed proximally extended zigzag stent comprised of struts and bends between the struts. Retention of such a stent graft onto an introducer can be by retention of the bends of the zigzag exposed stent to the introducer via a release mechanism. It is important, however, that the bends and struts of the exposed stent are retained onto the introducer in a neat manner to enable the stent graft to be radially compressed or constrained into as small as possible region and to allow for release without tangling of the bends and struts of the exposed stent.

Throughout this specification the term distal with respect to a portion of the aorta, a deployment device or a stent graft refers to the end of the aorta, deployment device or stent graft further away in the direction of blood flow away from the heart and the term proximal refers to the portion of the aorta, deployment device or end of the stent graft nearer to the heart. When applied to other vessels similar terms such as caudal and cranial should be understood.

SUMMARY OF THE INVENTION

In one form, therefore the invention is said to reside in a stent graft comprising a tubular body of a graft material and an exposed stent joined to and extending from one end of the tubular body, the exposed stent comprising a self expanding Z stent including a plurality of struts and bends therebetween, a pair of struts and a bend between the pair of struts defining an apex which is a selected apex distance to the bend away from the tubular body, wherein adjacent apices of the exposed stent are different distances to the bends from the tubular body.

Preferably there are three distances to the bends being a shorter distance, a medium distance and a longer distance and that the three distances to the bends are consecutively placed around the exposed stent. Hence if the exposed stent has twelve proximal apices then there would be four lots of three sets of the three distances to the bends.

There may be further included distally extending barbs on alternate struts of the exposed stent.

To facilitate packing on an introducer and to prevent tangling of the barbs upon release the barbs on alternate struts of the exposed stent may be spaced selected distances from their respective apices such that adjacent barbs are different distances from the apices.

In a further form the invention comprises a stent graft introducer and a stent graft releasably retained thereon, the introducer comprising a trigger wire catheter and a plurality of trigger wires and each trigger wire extending in a loop from the trigger wire catheter, the stent graft comprising a tubular body of a graft material and an exposed stent joined to and extending from one end of the tubular body, the exposed stent comprising a self expanding Z stent including a plurality of struts and bends therebetween, a pair of struts and a bend between defining an apex a selected distance to the bend away from the tubular body, wherein adjacent apices of the exposed stent are different distances to the bends from the tubular body, the stent graft being retained onto the introducer by the one trigger wire of the plurality of trigger wires passing through an apex of the exposed stent, wherein at least two apices of different distances to the bends from the tubular body are retained by the one trigger wire.

Preferably the introducer has four trigger wires so that three bends of a twelve bend exposed stent are retained by each trigger wire. There can be used a stent graft with different numbers of proximal bends on the exposed stent and the introducer can have different numbers of trigger wires to retain the proximal end of the stent graft to the introducer. For instance an exposed stent with nine proximal bends can be retained on a delivery device using three trigger wires with three bends each retained by each wire. An exposed stent with ten proximal bends can be retained on a delivery device using four trigger wires with two bends each retained by two of the wires and three bends each retained by the other two wires.

Hence, it will be seen that by this invention, an arrangement for retaining the bends of an exposed stent onto an introducer by the use of trigger wires is provided in which adjacent bends stack up one next to the other, preferably three bends to a trigger wire and thereby are retained in as small a volume as possible and can be released without problem.

Similarly, by placing the barbs spaced distances along alternate struts, the barbs have less tendency to engage with each other and cause problems during release.

This, then, generally describes the invention but to assist with understanding, reference will now be made to the accompanying drawings which show a preferred embodiment of the invention.

DETAILED DESCRIPTION

Figure 1:
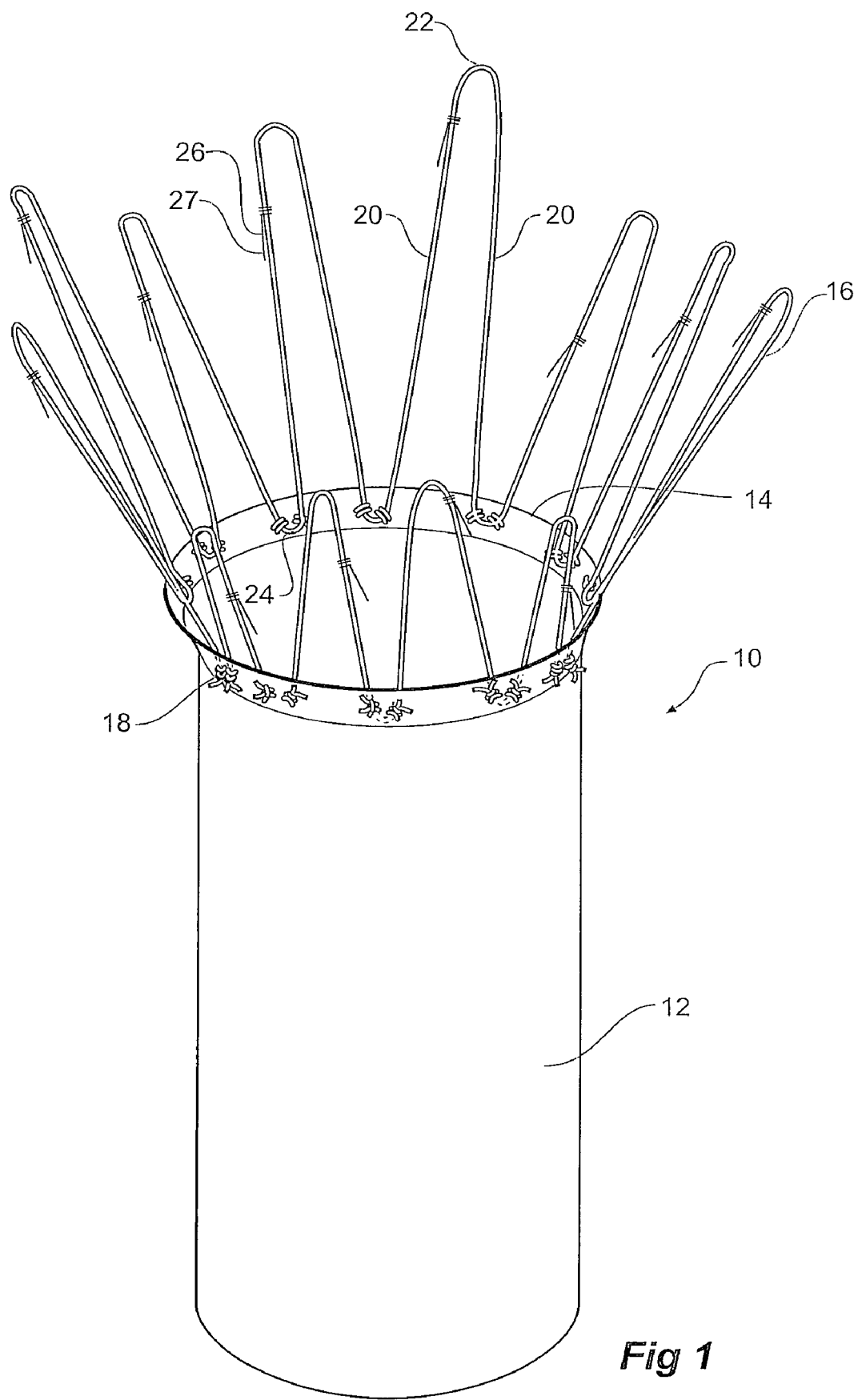
FIG. 1 shows a stent graft suitable for endovascular deployment and including an exposed zigzag stent at its proximal end according to one embodiment of the present invention.

Now looking more closely at the drawings and in particular FIG. 1, it will be seen that a stent graft 10 has a tubular body 12 of a biocompatible graft material. At the proximal end 14 of the stent graft an exposed zigzag stent 16 is fastened to the tubular body 12 by stitching 18 and extends away from the tubular body. The exposed self expanding stent 16 is formed from struts 20 of a resilient wire such as stainless steel with proximal bends 22, 26 and 30 and distal bends 24 between adjacent struts. The stitching 18 retaining the exposed stent to the proximal end of the stent graft is placed in the region of the distal bends 24. Barbs 26 are mounted onto alternate struts 20 with the point 27 of the barbs 26 extending distally. Further zig zag stents would normally be placed along the length of the stent graft but they have been omitted for clarity.

Figure 2:
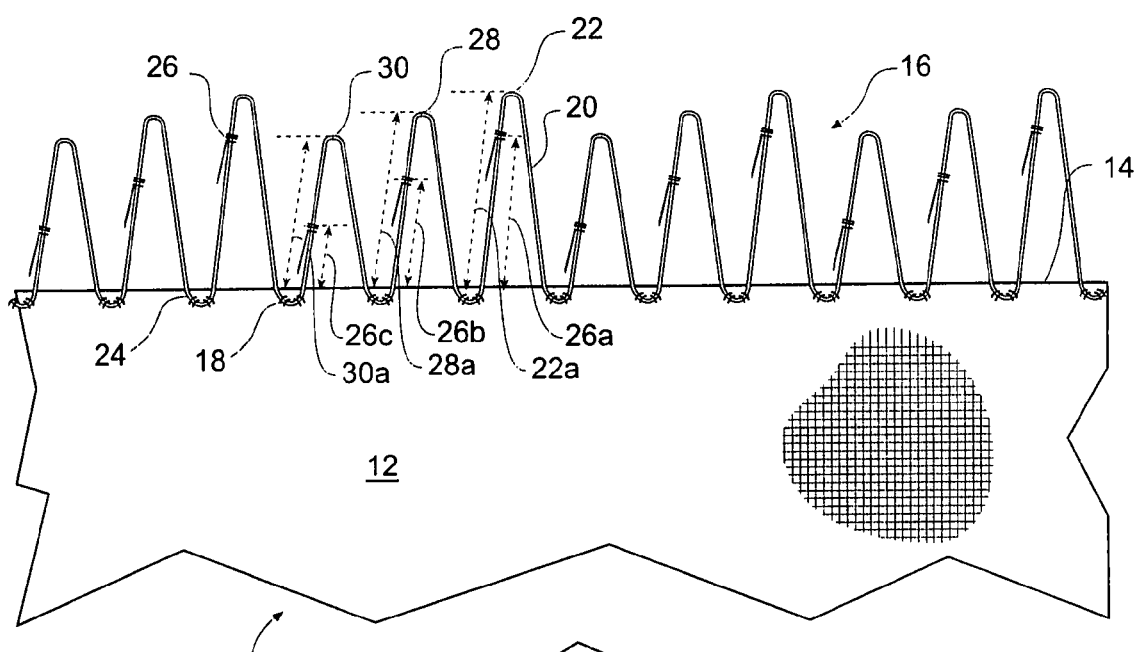
FIG. 2 shows a view of the proximal end of the stent of FIG. 1 with the stent graft laid out flat.

The proximal end 14 of the tubular body 12 of the stent graft 10 is shown in a laid out flat format in FIG. 2.

It can be seen in FIG. 2 that the bend 22 is the longest distance to the bend 22a from the tubular body 12, the adjacent bend 28 is a medium distance to the bend 28a from the tubular body 12 and the next adjacent bend 30 is the shortest distance to the bend 30a from the proximal end 14 of the tubular body 12. These three distances to the bends 22a, 28a and 30a are used consecutively around the proximal end of the tubular body.

It will also be noted that the barbs 26 on alternate struts 20 are spaced at different distances 26a, 26b and 26c from the proximal end 14 of the tubular body on adjacent alternate struts so as to assist in preventing adjacent barbs tangling or engaging with each other during introduction and release of the stent graft.

Figure 3:
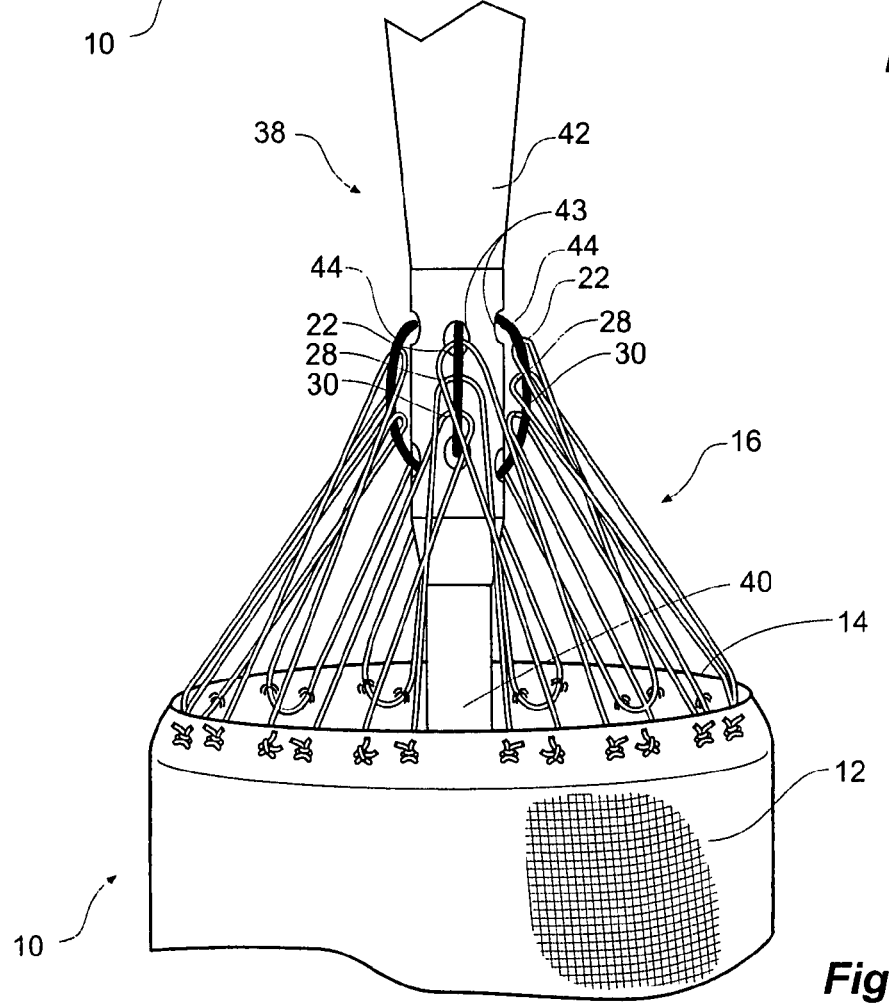
FIG. 3 shows the stent graft of FIGS. 1 and 2 in detail retained onto a stent graft introducer.

FIG. 3 shows the stent graft of FIGS. 1 and 2 in detail retained onto a stent graft introducer before it is radially compressed within a sheath for delivery. Only part of the introducer is shown in FIG. 3.

To retain the stent graft 10 onto an introducer 38 the exposed self expanding stent 16 is retained by trigger wires to the introducer. The introducer comprises a trigger wire catheter 40 extending to a nose cone dilator 42 with trigger wires 44 extending out of apertures 43 in the trigger wire catheter 40. In this embodiment there are four trigger wires 44. Each trigger wire 44 retains three proximal bends 22, 28 and 30 of the exposed stent 16.

It will be noted that adjacent individual bends 22, 28 and 30 of the exposed self expanding stent 16 are retained under a single trigger wire 44 and the bends being of different distances to the bends from the tubular body 12, they position neatly under the trigger wire and assist with stacking of the proximal end of the exposed stent 16 onto the introducer.

In a preferred embodiment of the invention the exposed self expanding stent 16 has adjacent pairs of struts with lengths of 26, 25 and 24 millimetres from the proximal end 14 of the tubular body 12, and the barbs are placed onto the alternate struts at distances of 4 to 7 mm, 7 to 10 mm and 10 to 13 mm from the respective bends of the exposed self expanding stent. Hence in one embodiment the barbs are spaced from the proximal end 14 of the tubular body 12 by distances of from 19 to 22 mm on the longest strut, 15 to 18 mm on the medium length strut and 11 to 14 mm on the shortest strut. All of these dimensions are measured along the struts and hence are at a slight angle to the longitudinal direction of the stent graft.

Figure 4A:
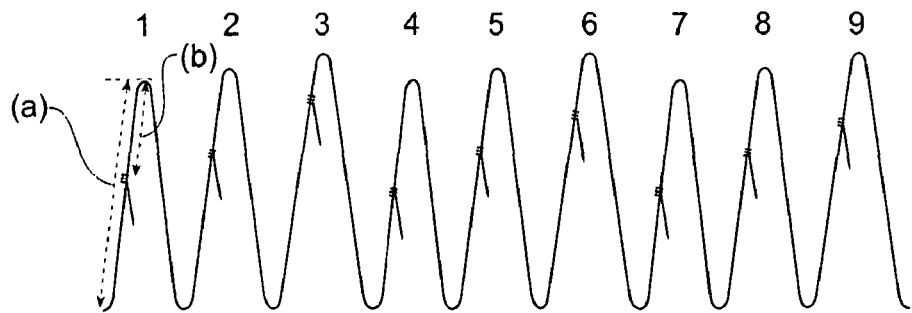
FIGS. 4A, 4B and 4C show strut lengths and barb spacings for stent with different numbers of bends or points according to one embodiment of the invention.
Figure 4B:
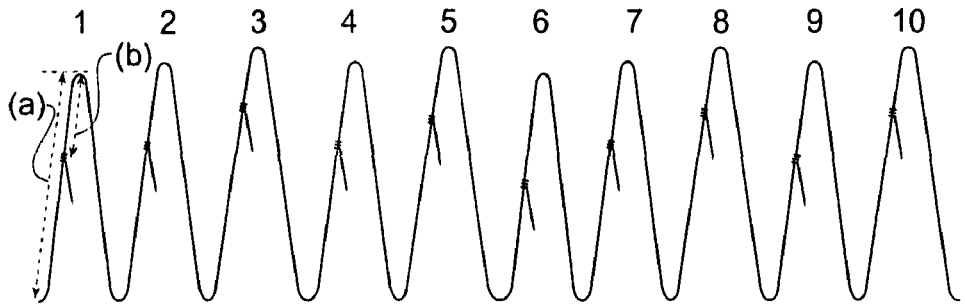
Figure 4C:
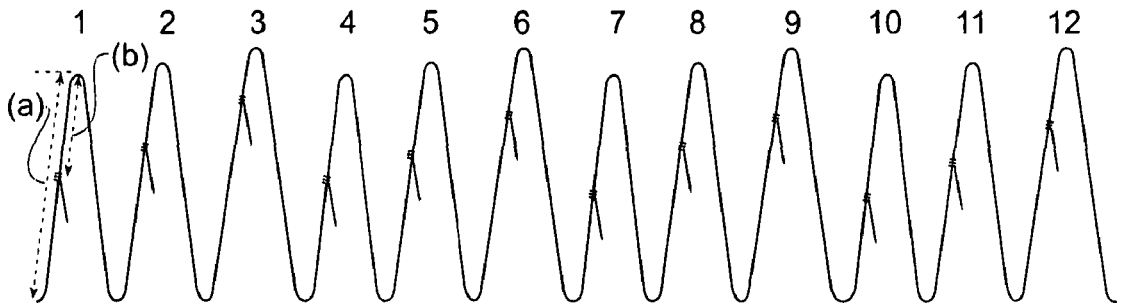

FIGS. 4A, 4B and 4C show strut lengths and barb spacings for stents with different numbers of bends or points according to one embodiment of the invention. FIG. 4A shows a stretched out stent with 9 proximal and 9 distal points or bends. FIG. 4B shows a stretched out stent with 10 proximal and 10 distal points or bends. FIG. 4C shows a stretched out stent with 12 proximal and 12 distal points or bends. The table accompanying each of FIGS. 4A, 4B and 4C show strut lengths and barb spacings for each point. All the dimensions are in millimetres. The length (a) in each of FIGS. 4A, 4B and 4C indicates the length of a strut of the stent and the length (b) in each of FIGS. 4A, 4B and 4C indicates the spacing of the barbs on alternate struts from the proximal point or bend. It will be noted that each strut is a different length than the strut on either side of it and that the barb spacing of adjacent barbs is different so that the barbs occupy as small a space as possible when the stent graft is compressed within a delivery sheath and are less likely to engage or tangle with each other.

Throughout this specification various indications have been given as to the scope of the invention but the invention is not limited to any one of these but may reside in two or more of these combined together. The examples are given only for illustration and not for limitation.

What is claimed is:

1. A stent graft introducer in combination with a stent graft, the stent graft releasably retained on the stent graft introducer, the introducer comprising a trigger wire catheter and a plurality of trigger wires and each trigger wire extending in a loop of a trigger wire from the trigger wire catheter, the stent graft comprising a tubular body of a graft material and an exposed stent joined to and extending from one end of the tubular body, the exposed stent comprising a self expanding Z stent including a plurality of struts and proximal and distal bends therebetween, the distal bends being joined to a proximal end of the tubular body, a pair of struts and a proximal bend defining an apex which is a selected distance to the proximal bend away from the tubular body, wherein adjacent apices of the exposed stent comprise different strut lengths thereby defining different distances to the respective proximal bend from the tubular body, the stent graft being retained onto the introducer by the trigger wires, the loop of a trigger wire of the plurality of trigger wires passing through at least two adjacent apices of different distances to the bends from the tubular body whereby the at least two adjacent apices are retained in a stacked configuration by the trigger wire.

2. A stent graft introducer and a stent graft releasably retained thereon as in claim 1 wherein there are three distances to the respective proximal bend being a shorter distance, a medium distance and a longer distance.

3. A stent graft introducer and a stent graft releasably retained thereon as in claim 2 wherein the three distances to the respective proximal bend are consecutively around the exposed stent.

4. A stent graft introducer and a stent graft releasably retained thereon as in claim 2 wherein the exposed stent has twelve apices comprising four sets of the three distances to the respective proximal bend consecutively around the exposed stent.

5. A stent graft as in claim 1 further including distally extending barbs on alternate struts of the exposed stent.

6. A stent graft as in claim 5 wherein the barbs on alternate struts of the exposed stent are spaced selected distances from their respective apices such that adjacent barbs are different distance from the apices.

* * * * *